United States Patent
Kadlec et al.

(10) Patent No.: US 9,714,323 B2
(45) Date of Patent: *Jul. 25, 2017

(54) CROSS-LINKED COMPOSITION AND METHOD OF FORMING THE SAME

(71) Applicant: Dow Corning Corporation, Midland, MI (US)

(72) Inventors: Donald A. Kadlec, Midland, MI (US); Kimmai T. Nguyen, Midland, MI (US); Kenneth E. Zimmerman, Midland, MI (US)

(73) Assignee: DOW CORNING CORPORATION, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/912,177

(22) PCT Filed: Oct. 29, 2014

(86) PCT No.: PCT/US2014/062873
§ 371 (c)(1),
(2) Date: Feb. 16, 2016

(87) PCT Pub. No.: WO2015/066161
PCT Pub. Date: May 7, 2015

(65) Prior Publication Data
US 2016/0200876 A1    Jul. 14, 2016

Related U.S. Application Data

(60) Provisional application No. 61/898,022, filed on Oct. 31, 2013, provisional application No. 61/898,027, (Continued)

(51) Int. Cl.
| | | |
|---|---|---|
| C08G 77/38 | (2006.01) | |
| C08G 77/26 | (2006.01) | |
| A61K 8/89 | (2006.01) | |
| C08L 83/06 | (2006.01) | |
| A61Q 19/00 | (2006.01) | |
| C08G 77/46 | (2006.01) | |

(52) U.S. Cl.
CPC .............. C08G 77/26 (2013.01); A61K 8/89 (2013.01); A61Q 19/00 (2013.01); C08G 77/38 (2013.01); C08L 83/06 (2013.01); A61K 2800/10 (2013.01); C08G 77/46 (2013.01)

(58) Field of Classification Search
None
See application file for complete search history.

(56) References Cited

U.S. PATENT DOCUMENTS 4,395,527 A    7/1983  Berger
4,605,567 A    8/1986  Muller et al.
(Continued)

FOREIGN PATENT DOCUMENTS

DE    3618714 A1    11/1987
EP    1900765        3/2008
(Continued)

OTHER PUBLICATIONS

English language abstract and machine-assisted English translation for EP1900765(A1) extracted from http://worldwide.espacenet.com on Jan. 13, 2017, 21 pages.
English language abstract and machine-assisted English translation for DE3618714(A1) extracted from http://worldwide.espacenet.com on Jan. 13, 2017, 14 pages.
PCT/US2014/062873 International Search Report dated Jan. 22, 2015, 3 pages.
PCT/US2014/062877 International Search Report dated Jan. 20, 2015, 4 pages.
PCT/US2014/062942 International Search Report dated Feb. 11, 2015, 4 pages.
(Continued)

*Primary Examiner* — Marc Zimmer
(74) *Attorney, Agent, or Firm* — Warner Norcross & Judd LLP

(57) ABSTRACT

A cross-linked composition comprises the reaction product of siloxanes having pendant anhydride groups and a reactant having hydroxyl and/or amine functional groups. The cross-linked composition can be of the following general formula (I): (I). Refer to formula (1) Each X can be of the following general formula (i): (i). Refer to formula (i) Each of W and W* is independently an oxygen atom or N—R, with R independently being a hydrogen atom or $R^1$. Each of Y, $R^3$, and $R^{13}$ is an independently selected divalent group. Each of $R^1$, $R^{11}$, $R^4$, $R^{14}$, $R^5$, and $R^{15}$ is an independently selected substituted or unsubstituted hydrocarbyl group. Each of w and ww, and each of y and yy, is an independently selected integer from 0 to 1,000. Each of x and xx is an independently selected integer from 1 to 100. Typically, w and y are not simultaneously 0, and ww and yy are not simultaneously 0.

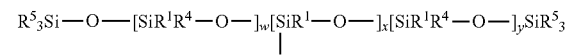

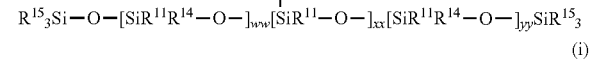

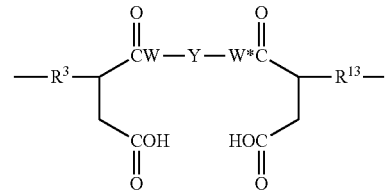

20 Claims, No Drawings

Related U.S. Application Data filed on Oct. 31, 2013, provisional application No. 61/898,029, filed on Oct. 31, 2013, provisional application No. 61/898,033, filed on Oct. 31, 2013.

(56) References Cited

U.S. PATENT DOCUMENTS

| | | | |
|---|---|---|---|
| 4,658,049 A | 4/1987 | Nakano et al. | |
| 4,794,153 A | 12/1988 | Rich | |
| 4,795,680 A * | 1/1989 | Rich | C08G 73/106 257/791 |
| 4,876,152 A * | 10/1989 | Kang | C04B 41/009 427/387 |
| 4,945,148 A | 7/1990 | Rich et al. | |
| 4,987,169 A | 1/1991 | Kuwata et al. | |
| 5,015,700 A | 5/1991 | Herzig et al. | |
| 5,236,986 A | 8/1993 | Sakuta | |
| 5,247,111 A | 9/1993 | O'Lenick, Jr. | |
| 5,248,783 A | 9/1993 | O'Lenick | |
| 5,272,241 A | 12/1993 | Lucarelli et al. | |
| 5,280,019 A | 1/1994 | Klimisch | |
| 5,385,999 A | 1/1995 | D'Anvers et al. | |
| 5,412,074 A | 5/1995 | Jones et al. | |
| 5,596,061 A | 1/1997 | Berger et al. | |
| 5,637,746 A | 6/1997 | Knebelkamp et al. | |
| 5,654,362 A | 8/1997 | Schulz, Jr. et al. | |
| 5,686,011 A | 11/1997 | Lohmann et al. | |
| 5,702,490 A | 12/1997 | Kneip et al. | |
| 5,736,583 A | 4/1998 | Berger et al. | |
| 5,760,116 A | 6/1998 | Kilgour et al. | |
| 5,811,487 A | 9/1998 | Schulz, Jr. et al. | |
| 5,854,356 A * | 12/1998 | Bergstrom | C08F 8/42 525/101 |
| 5,880,210 A | 3/1999 | Schulz, Jr. et al. | |
| 5,902,360 A * | 5/1999 | Linzell | B24B 31/116 428/447 |
| 5,929,162 A | 7/1999 | Horne et al. | |
| 5,969,035 A | 10/1999 | Meinhardt et al. | |
| 6,007,801 A | 12/1999 | Hossel et al. | |
| 6,020,409 A | 2/2000 | Alvarez et al. | |
| 6,110,230 A | 8/2000 | Friedrich et al. | |
| 6,124,490 A | 9/2000 | Gormley et al. | |
| 6,200,581 B1 | 3/2001 | Lin et al. | |
| 6,238,657 B1 | 5/2001 | Lin et al. | |
| 6,262,170 B1 | 7/2001 | Kilgour et al. | |
| 6,271,295 B1 | 8/2001 | Powell et al. | |
| 6,355,724 B1 | 3/2002 | LeGrow et al. | |
| 6,365,670 B1 | 4/2002 | Fry | |
| 6,423,322 B1 | 7/2002 | Fry | |
| 6,444,745 B1 | 9/2002 | Kilgour et al. | |
| 6,455,640 B2 | 9/2002 | Okawa | |
| 6,503,519 B1 | 1/2003 | Sakuta | |
| 6,531,540 B1 | 3/2003 | O'Brien | |
| 6,538,061 B2 | 3/2003 | Chaiyawat et al. | |
| 6,565,837 B2 | 5/2003 | Fost et al. | |
| 6,602,947 B2 | 8/2003 | Merz et al. | |
| 6,653,378 B2 | 11/2003 | Ferritto et al. | |
| 6,716,908 B2 | 4/2004 | Lomas et al. | |
| 6,747,115 B2 | 6/2004 | Sakuta | |
| 6,770,708 B2 | 8/2004 | Kadlec et al. | |
| 6,797,742 B2 | 9/2004 | Kilgour et al. | |
| 6,838,541 B2 | 1/2005 | Lin et al. | |
| 6,881,416 B2 | 4/2005 | Fry | |
| 6,887,836 B2 | 5/2005 | Majeti et al. | |
| 7,019,098 B2 | 3/2006 | Hupfield | |
| 7,163,674 B2 | 1/2007 | Majeti et al. | |
| 7,166,276 B2 | 1/2007 | Stephens et al. | |
| 7,241,835 B2 | 7/2007 | O'Brien et al. | |
| 7,279,223 B2 | 10/2007 | Rubinsztajn et al. | |
| 7,413,744 B2 | 8/2008 | Ichinohe | |
| 7,790,827 B2 | 9/2010 | Nguyen et al. | |
| 8,013,094 B2 | 9/2011 | Okawa et al. | |
| 8,026,330 B2 | 9/2011 | Kamei | |
| 8,110,630 B2 | 2/2012 | Lin et al. | |
| 8,147,854 B2 | 4/2012 | Okawa et al. | |
| 8,273,840 B2 | 9/2012 | Lin | |
| 8,338,630 B2 | 12/2012 | Moriya | |
| 8,398,964 B2 | 3/2013 | Kamei et al. | |
| 8,455,603 B2 | 6/2013 | Ferenz et al. | |
| 8,586,669 B2 | 11/2013 | Kennan et al. | |
| 8,653,190 B2 | 2/2014 | Chatterjee et al. | |
| 8,912,354 B2 | 12/2014 | Kamei | |
| 8,920,783 B2 | 12/2014 | Lin | |
| 9,243,113 B2 | 1/2016 | Ahn et al. | |
| 2003/0082129 A1 | 5/2003 | Buckingham et al. | |
| 2004/0138376 A1 | 7/2004 | Awad | |
| 2004/0234477 A1 | 11/2004 | Sukuta | |
| 2006/0127338 A1 | 6/2006 | Morita et al. | |
| 2008/0076886 A1 | 3/2008 | Burns et al. | |
| 2009/0317343 A1 | 12/2009 | Lin et al. | |
| 2010/0135916 A1 | 6/2010 | Courel et al. | |
| 2010/0215595 A1 | 8/2010 | Kennan et al. | |
| 2010/0233104 A1 | 9/2010 | Drake et al. | |
| 2010/0303743 A1 | 12/2010 | Kennan et al. | |
| 2010/0330011 A1 | 12/2010 | Kennan et al. | |
| 2011/0052523 A1 | 3/2011 | Moriya et al. | |
| 2012/0219517 A1 | 8/2012 | Ahn et al. | |
| 2013/0041084 A1 | 2/2013 | Chatterjee et al. | |
| 2016/0194456 A1 | 7/2016 | Kadlec et al. | |
| 2016/0199286 A1 * | 7/2016 | Mary Kay | A61Q 19/00 424/60 |

FOREIGN PATENT DOCUMENTS

| | | |
|---|---|---|
| EP | 1900765 A1 | 3/2008 |
| EP | 2418236 A1 | 2/2012 |
| JP | 2740590 | 1/1998 |
| JP | 2003146832 | 5/2003 |
| JP | 2003292415 | 10/2003 |
| JP | 3678420 B2 | 8/2005 |
| JP | 2010265338 | 11/2010 |
| WO | 03041664 | 5/2003 |
| WO | 2015066161 | 5/2015 |
| WO | 2015066165 | 5/2015 |
| WO | 2015066199 | 5/2015 |

OTHER PUBLICATIONS

English language abstract and machine-assisted English translation for JP3678420(B2) extracted from https://patents.google.com on Jan. 13, 2017, 57 pages.

\* cited by examiner

CROSS-LINKED COMPOSITION AND METHOD OF FORMING THE SAME

This application is a national stage entry of International Patent Application No. PCT/US2014/62873, filed Oct. 29, 2014, which claims the benefit of U.S. Provisional Patent Application Nos. 61/898,022, 61/898,027, 61/898,029, and 61/898,033, each filed on Oct. 31, 2013, the disclosures of which are incorporated by reference.

The present invention generally relates to a cross-linked composition comprising the reaction product of siloxanes having anhydride groups and a reactant having functional groups reactive with the anhydride groups. The functional groups of the reactant are at least one of hydroxyl groups or amine groups. The present invention also generally relates to a method of forming the cross-linked composition.

Silicone elastomer gels/blends have been used extensively to enhance the aesthetics of personal care formulations for skincare and healthcare by providing a unique sensory profile upon application. For example, such gels/blends can provide sensory characteristics such as a velvety, silky or powdery feel. In addition, such gels/blends are also valued for providing rheology modification to personal care (e.g. skin, sun, cosmetic) and healthcare formulations.

Most silicone elastomer gels are obtained by a cross-linking hydrosilylation reaction of a SiH functional polysiloxane with another polysiloxane containing an unsaturated hydrocarbon substituent, such as a vinyl functional polysiloxane, or by cross-linking a SiH functional polysiloxane with a hydrocarbon diene or with a terminally unsaturated polyoxyalkylene (e.g. PEG/PPG). These silicone elastomer gels are compatible with mostly non-polar organic solvents. Unfortunately, such silicone elastomer gels have limited versatility in formulations with polar solvents such as hydrocarbon oils, ester oils and plant based oils. In view of the foregoing, there remains an opportunity to provide silicones with increased formulation versatility, as well as to provide silicones having excellent aesthetic and rheological properties.

BRIEF SUMMARY OF THE INVENTION

Disclosed is a cross-linked composition. The cross-linked composition comprises the reaction product of a first siloxane having at least one pendant anhydride group, a second siloxane having at least one pendant anhydride group, and a reactant having functional groups reactive with the anhydride groups of the first and second siloxanes.

The reactant is generally selected from the group of an organic polyol, an organic polyamine, a third siloxane, or combinations thereof. The organic polyol has at least two hydroxyl groups. The organic polyamine has at least two amine groups. The third siloxane can have at least two hydroxyl groups or at least two amine groups. In a first embodiment of the disclosure, the reactant comprises the organic polyol. Other embodiments of the disclosure use one or more of the other reactants in addition or alternate to the organic polyol.

Typically, the cross-linked composition is of the following general formula (I):

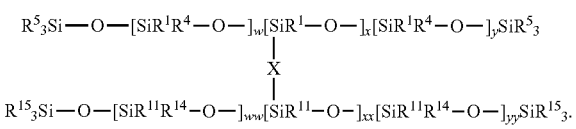

Each X is of the following general formula (i):

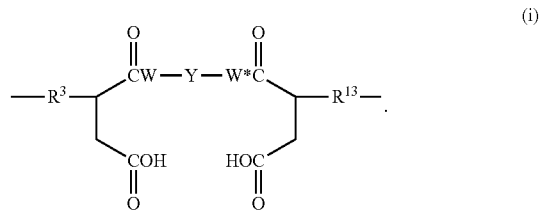

Each of W and W* is independently an oxygen atom (O) or N—R, with R independently being a hydrogen atom (H) or $R^1$. Each Y is a divalent group. In the first embodiment of the disclosure, each of W and W* is independently an O, and Y is an organic divalent group. Each of $R^1$, $R^{11}$, $R^4$, $R^{14}$, $R^5$, and $R^{15}$ is an independently selected substituted or unsubstituted hydrocarbyl group. Each of $R^3$ and $R^{13}$ is an independently selected divalent group. Each of w and ww is an independently selected integer from 0 to 1,000. Each of x and xx is an independently selected integer from 1 to 100. Each of y and yy is an independently selected integer from 0 to 1,000. Typically, w and y are not simultaneously 0, and ww and yy are not simultaneously 0. As shown in formula (i), the cross-linked composition generally has at least two carboxyl groups.

Also disclosed is a method of forming the cross-linked composition. The method comprises the steps of providing the first siloxane, providing the second siloxane, and providing the reactant. The method further comprises the step of combining the first siloxane, second siloxane, and reactant to form the cross-linked composition.

DETAILED DESCRIPTION OF THE INVENTION

Disclosed are a cross-linked composition ("composition") and a method of forming the composition ("method"). The composition comprises the reaction product of a first siloxane, a second siloxane, and a reactant. The first and second siloxanes are referred to collectively as "the siloxanes". In certain embodiments, the composition consists essentially of the reaction product of the siloxanes and reactant. In further embodiments, the composition consists of the reaction product of the siloxanes and reactant. In certain embodiments, the composition can include one or more siloxanes in addition to, and different from, the first and second siloxanes (and different from third siloxanes described below).

In a first general embodiment of the disclosure ("first embodiment"), the reactant comprises an organic polyol. In the first embodiment, the reactant may also consist essentially of, or consist of, the organic polyol. In a second general embodiment of the disclosure ("second embodiment"), the reactant comprises an organic polyamine. In the second embodiment, the reactant may also consist essentially of, or consist of, the organic amine. In a third general embodiment of the disclosure ("third embodiment"), the reactant comprises a third siloxane having at least two hydroxyl groups. In the third embodiment, the reactant may also consist essentially of, or consist of the third siloxane, which may also be referred to as a hydroxyl functional siloxane. In a fourth general embodiment of the disclosure ("fourth embodiment"), the reactant comprises a third siloxane having at least two amine groups. In the fourth embodiment, the reactant may also consist essentially of, or consist of, the third siloxane, which may also be referred to as an amine functional siloxane. In further embodiments, the reactant comprises a combination of two or more of the aforementioned components, e.g. the polyol and polyamine, the hydroxyl and amine functional siloxanes, the polyol and hydroxyl functional siloxane, etc.

The first siloxane has at least one pendant anhydride group. The second siloxane also has at least one pendant anhydride group. Pendant groups may also be referred to as side groups, and are different from terminal groups sometimes referred to as end groups. Each of the siloxanes is generally free of terminal anhydride groups. Typically, each of the anhydride groups is directly bonded to an intervening atom or linkage that is directly bonded to a silicon atom. The anhydride groups are useful for reaction with the reactant, and can also impart additional functionality to the composition. It is thought that potential benefits provided by, or attributable to, the anhydride groups include, but are not limited to, film forming, substantivity, durability, pigment/particle suspension and/or modification, long lasting/wear, additional chemistry, actives (e.g. drug) or inactives (e.g. fragrance) delivery/release, hydrophilicity, reactivity, compatibility, polarity, and combinations thereof. In certain embodiments, the anhydride groups can provide free carboxyl groups, which can also provide benefits and/or be available for a subsequent, non-limiting reaction. In other embodiments, the composition may have one or more free anhydride groups for a subsequent, non-limiting reaction.

The reactant has at least two functional groups reactive with the pendant anhydride groups of the siloxanes. In the first and third embodiments, the functional groups are hydroxyl groups, whereas in the second and fourth embodiments, the functional groups are amine groups. Each of the functional groups of the reactant can be pendant or terminal. In various embodiments, the reactant has two functional groups, e.g. two hydroxyl groups or two amine groups.

Each of the siloxanes can be chemically (or physically) the same, such as two separate molecules of the same siloxane component (or type). For example, the siloxanes can be provided together, such as in an "A-part" (or A-side) of a system for forming the composition. Alternatively, the siloxanes can be provided separately, especially when they are different from each other. This may be useful for formulation purposes. However, separation is not required, as the siloxanes are typically inert with respect to each other.

The reactant can be provided separate from the siloxanes, such as in a "B-part" (or B-side) of a system for forming the composition. If the composition includes one or more optional additives, the additive(s) can be included with either of, each of, or a combination of, the system parts. The system may include more than two parts. Optionally, various types of conventional additives can be utilized depending, for example, on the end use of the composition. The disclosure is not limited to any particular arrangement of the system, or to any particular additive or additives. The siloxanes are described in greater detail below.

The Siloxanes

In various embodiments, each of the siloxanes consists of siloxane bonds (Si—O—Si) within each of their backbones. Alternatively, each of the siloxanes may include siloxane bonds separated by one or more divalent groups, e.g. a —CH$_2$— linking group. Further examples of suitable divalent groups include polyether groups, e.g. a —CH$_2$CH$_2$O— linking group (i.e., an EO group), a —CH(CH$_3$)CH$_2$O— linking group (i.e., a PO group), etc. Combinations of different divalent groups may be present within each of their backbones. Each of the divalent groups may be singular or repeated, e.g. 2 times, 5 times, 10 times, >10 times, etc. In certain embodiments, the siloxanes are free of polyether groups.

In various embodiments, each of the siloxanes comprise at least one [SiR$^1$R$^2$—O—] unit ("D" or R*$_2$SiO$_{2/2}$ units). Typically, each of the siloxanes has repeating D units, which generally constitute linear portions of the siloxanes. The siloxanes also typically have terminal R*$_3$SiO$_{1/2}$ units ("M" units).

In certain embodiments, each of the siloxanes may optionally be branched, partially branched, and/or may include a resinous portion having a three-dimensional networked structure. In such embodiments, the respective siloxane may further comprise R*SiO$_{3/2}$ units ("T" units) and/or SiO$_{4/2}$ units ("Q" units). Branching of the siloxane itself, or the resinous portion of the siloxane, if present, can be attributable to the presence of T and/or Q units. Branching may also be attributable to side groups of one or more D units. In various embodiments, the siloxanes are free of T units, Q units, or both T and Q units. The siloxanes can be the same or different, e.g. one is linear and one is branched, both are branched, both are linear, etc.

With reference to the [SiR$^1$R$^2$—O—] unit, R$^1$ is an independently selected substituted or unsubstituted hydrocarbyl group. By "substituted," it is meant that one or more hydrogen atoms of the hydrocarbon may be replaced with atoms other than hydrogen (e.g. a halogen atom), or a carbon atom within the chain of R$^1$ may be replaced with an atom other than carbon, i.e., R$^1$ may include one or more heteroatoms within the chain, such as oxygen, sulfur, nitrogen, etc. Examples of suitable hydrocarbyl groups represented by R$^1$ include alkyl, aryl, alkenyl, alkaryl, and aralkyl, groups.

In certain embodiments, R$^1$ is an independently selected alkyl group typically having from 1 to 20, 1 to 15, 1 to 10, 1 to 6, 1 to 4, or 1 to 2, carbon atoms, or any number of carbon atoms in between. Specific examples of suitable alkyl groups as R$^1$ include methyl groups, ethyl groups, propyl groups, butyl groups, pentyl groups, etc. Typically, R$^1$ is a methyl group (i.e., —CH$_3$).

R$^2$ is a pendant anhydride group of the following general formula (A):

(A)

where R$^3$ is a divalent group. Typically, R$^3$ is a hydrocarbylene, heterohydrocarbylene, or organoheterylene group. In various embodiments, R$^3$ is (CH$_2$)$_n$ where n is an integer selected from 1 to 30, 1 to 25, 1 to 20, 1 to 15, 1 to 10, 1 to 5, or 1 to 3, or any number in between. Typically, n is 3.

In various embodiments, each of the siloxanes is individually of the following general formula (B):

(B).

In further embodiments, each of the siloxanes is individually of the following general formula (B1):

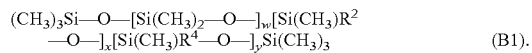

(B1).

In formulas (B) and (B1), each of $R^1$ and $R^2$ are as described above. $R^4$ can be of various chemistries, including organic, inorganic, and combinations thereof. In various embodiments, each of $R^4$ and $R^5$ can be an independently selected substituted or unsubstituted hydrocarbyl group. Examples of suitable groups for each of $R^4$ and $R^5$ are as described for $R^1$. In certain embodiments, each $R^4$ is an independently selected alkyl group, aryl group, or $(R^6O)_m$ group. If $R^4$ is a $(R^6O)_m$ group, $R^6$ is typically an alkyl group or aryl group and m is an integer selected from 1 to 50, 1 to 25, 1 to 10, 1 to 5, or 1, or any number in between. The $(R^6O)_m$ group may also be referred to as a polyether group. In specific embodiments, $R^4$ is an independently selected alkyl group having from 2 to 20, 2 to 15, 2 to 10, 2 to 5, or 2, carbon atoms, or any number of carbon atoms in between. Without being bound or limited by any particular theory, it is thought that the organic compatibility of the composition, e.g. in a solvent, can be enhanced by having a long chain alkyl group on one or both of the siloxane backbones, e.g. as $R^4$. In alternate embodiments, $R^4$ may be silicone side chain of the siloxane. The groups represented by subscripts w, x, and y, i.e., the groups having square brackets in formulas (B) and (B1), may be present in any order within the respective siloxane, including a different order than that which is represented above and throughout this disclosure. Moreover, these groups may be present in randomized or block form.

Typically, $R^4$ is either an alkyl group or a polyether group. Without being bound or limited to any particular theory, it is thought that the hydrophilic character of the composition can be enhanced by having a polyether side chain (or chains) on one or both of the siloxane backbones, e.g. as $R^4$. Typically, each $R^5$ is $R^1$. For example, each of $R^1$ and $R^5$ can be an alkyl group, e.g. a methyl group.

Typically, w is an integer selected from 0 to 1,000, 0 to 950, 0 to 750, 0 to 500, 0 to 400, 1 to 350, 1 to 300, 25 to 250, 50 to 200, 50 to 150, 75 to 125, 90 to 110, 90 to 100, or 90 to 95, or any number in between. In a specific embodiment, w is 93. Typically, x is an integer selected from 1 to 100, 1 to 75, 1 to 50, 1 to 25, 1 to 20, 1 to 10, or 1 to 5, or any number in between. In a specific embodiment, x is 3. Typically, y is an integer selected from 0 to 1,000, 0 to 950, 0 to 750, 0 to 500, 0 to 400, 1 to 350, 1 to 300, 1 to 250, 1 to 200, 1 to 150, 1 to 100, 1 to 75, 1 to 50, 1 to 25, 1 to 20, 1 to 15, 1 to 10, or 1 to 5, or any number in between.

In various embodiments, w and y are not simultaneously 0. Said another way, in these embodiments, each of the siloxanes include at least one D unit associated with each of the x units and at least one of the w and y units in formula (B). In certain embodiments, the sum of w+x+y is from 25 to 1,500, 25 to 1,000, 25 to 900, 25 to 800, 25 to 700, 25 to 600, 25 to 500, 25 to 400, 25 to 300, 50 to 200, 75 to 150, 85 to 125, or 90 to 110, or any number in between. In these embodiments, x is at least 1, at least 10, at least 25, at least 50, at least 75, or at least 85. In this way, each of the siloxanes has at least one of the pendant anhydride groups, and can have other side groups based on the presence of one or more D units associated with w and y. Embodiments of the reactant are described in greater detail below.

First Embodiment

Typically, the organic polyol has two terminal hydroxyl groups and is free of pendant hydroxyl groups. Each of the hydroxyl groups can be directly bonded to a carbon atom, or to an intervening atom or linkage that is directly bonded to a carbon atom. Each of the hydroxyl groups can be primary, secondary, or tertiary, typically primary or secondary, more typically primary. The hydroxyl groups are useful for reaction with the siloxanes, and can also impart additional functionality to the composition. Typically, all of the hydroxyl groups of the organic polyol cross-link with anhydride groups of the siloxanes to form linkages (e.g. ester cross-links). Some amount of anhydride and/or carboxyl groups can remain free depending on the amount of hydroxyl groups present during reaction to form the composition. Such free groups can be useful for subsequent reaction(s) and/or can also interact with substrate surfaces, e.g. skin, leather, etc.

The organic polyol can be any type of polyol provided it has at least two hydroxyl groups reactive with the pendant anhydride groups of the siloxanes. In this way, the organic polyol serves as a cross-linker between the siloxanes to thereby form the composition. The composition may constitute just one molecule of the organic polyol, or a plurality of molecules of the organic polyol depending, for example, on the number of pendant anhydride groups attributable to the siloxanes. In certain embodiments, the composition can include one or more polyols in addition to, and different from, the organic polyol.

By "organic", it is generally meant that the organic polyol contains predominantly carbon, e.g. a carbon backbone. While carbon is present, other atoms may also be present, such as oxygen atoms, hydrogen atoms, nitrogen atoms, etc. In many embodiments, the organic polyol is free of silicon, e.g. one or more silicon (Si) atoms.

In various embodiments, the organic polyol ("polyol") is a diol (i.e., the polyol has two hydroxyl groups). Examples of suitable diols include, but are not limited to, methylene glycol, ethylene glycol, diethylene glycol, propylene glycol, dipropylene glycol, butane diol, bisphenol A, 1,4-butanediol, 1,3-propanediol, 1,5-pentanediol, 1,7-heptanediol, 1,2-hexanediol, triethylene glycol, tripropylene glycol neopentyl glycol, and combinations thereof. In other embodiments, the polyol is a triol (i.e., the polyol has three hydroxyl groups).

In many embodiments, the polyol has the following general formula HO—$R^7$—OH. $R^7$ may comprise at least one of a hydrocarbylene, a heterohydrocarbylene, or an organoheterylene group. In these embodiments, $R^7$ is typically selected from alkyl, cycloalkyl, alkyl cycloalkyl, aromatic, and alkylaromatic diradicals. Such diradicals generally have up to 50, up to 40, up to 30, up to 20, or up to 10, carbon atoms, or any number of carbon atoms between 1 and 50. The carbon chain which makes up the backbone of the polyol may be straight chained or branched. In certain embodiments, the polyol may have ether, thio, or amine linkages in its main chain. In specific embodiments, $R^7$ is a hydrocarbylene group having from 1 to 40, 1 to 30, 1 to 20, or 1 to 10 carbon atoms, or any number of carbon atoms in between.

In certain embodiments, the polyol is a (poly)oxyalkylene compound. Suitable examples of such compounds include, but are not limited to, ethylene glycol, diethylene glycol, triethylene glycol, polyethylene glycol (e.g. having a molecular weight of 200 to 2,000), propylene glycol, dipropylene glycol, polypropylene glycol (e.g. having a molecular weight of 200 to 3,000), butylene glycol, dibutylene glycol, polybutylene glycol (e.g. having a molecular weight of 200 to 4,000), random copolymers and block copolymers of polyethylenepropylene glycol (e.g. having a molecular weight of 100 to 3,000), random copolymers and block copolymers of polyethylenebutylene glycol (e.g. having a molecular weight of 100 to 4,000), and combinations thereof.

In various embodiments, the polyol can comprise a polyester polyol, a polyether polyol, a polyether/ester polyol, or combinations thereof. Furthermore, the polyol may be selected from aliphatic polyols, cycloaliphatic polyols, aromatic polyols, heterocyclic polyols, and combinations thereof. Some examples of suitable polyols include, but are not limited to, glycol-initiated polyols, glycerine-initiated polyols, sucrose-initiated polyols, sucrose/glycerine-initiated polyols, trimethylolpropane-initiated polyols, and combinations thereof.

Suitable polyester polyols include hydroxyl-terminated reaction products of polyhydric alcohols, polyester polyols obtained by the polymerization of lactones, e.g. caprolactone, in conjunction with a polyol, and polyester polyols obtained by the polymerization of hydroxy carboxylic acids, e.g. hydroxy caproic acid. Polyesteramide polyols, polythioether polyols, polycarbonate polyols, polyacetal polyols, and polyolefin polyols may also be used.

Suitable polyether polyols include products obtained by the polymerization of a cyclic oxide, such as ethylene oxide (EO), propylene oxide (PO), butylene oxide (BO), and tetrahydrofuran in the presence of a polyfunctional initiator. Suitable initiator compounds contain a plurality of active hydrogen atoms, and include, but are not limited to, water, butanediol, ethylene glycol, propylene glycol, diethylene glycol, triethylene glycol, dipropylene glycol, ethanolamine, diethanolamine, triethanolamine, toluene diamine, diethyl toluene diamine, phenyl diamine, diphenylmethane diamine, ethylene diamine, cyclohexane diamine, cyclohexane dimethanol, resorcinol, bisphenol A, glycerol, trimethylolpropane, 1,2,6-hexanetriol, pentaerythritol, and combinations thereof. Some of these initiators may also be useful as the polyol itself. In specific embodiments, the polyol is a polyether diol. Combinations of different polyols can be utilized to form the composition. Optionally, the polyol may contain one or more Si atoms.

Second Embodiment

Typically, the organic polyamine has two terminal amine groups and is free of pendant amine groups. Each of the amine groups can be directly bonded to a carbon atom, or to an intervening atom or linkage that is directly bonded to a carbon atom. Each of the amine groups can be primary or secondary, typically primary. The amine groups are useful for reaction with the siloxanes, and can also impart additional functionality to the composition. Typically, all of the amine groups of the polyamine cross-link with anhydride groups of the siloxanes to form linkages. Some amount of anhydride and/or carboxyl groups can remain free depending on the amount of amine groups present during reaction to form the composition. Such free groups can be useful for subsequent reaction(s), and/or can also interact with substrate surfaces, e.g. skin, leather, etc.

The organic polyamine can be any type of polyamine provided it has at least two amine groups reactive with the pendant anhydride groups of the siloxanes. In this way, the organic polyamine serves as a cross-linker between the siloxanes to thereby form the composition. The composition may constitute just one molecule of the organic polyamine, or a plurality of molecules of the organic polyamine depending, for example, on the number of pendant anhydride groups attributable to the siloxanes. In certain embodiments, the composition can include one or more polyamines in addition to, and different from, the organic polyamine.

By "organic", it is generally meant that the organic polyamine contains predominantly carbon, e.g. a carbon backbone. While carbon is present, other atoms may also be present, such as oxygen atoms, hydrogen atoms, nitrogen atoms, etc. In many embodiments, the organic polyamine is free of silicon, e.g. one or more Si atoms.

In various embodiments, the organic polyamine ("polyamine") is a diamine (i.e., the polyamine has two amine groups). Examples of suitable diamines include, but are not limited to, ethylenediamine, toluene diamine, 1,3-diaminopropane, putrescine, cadaverine, hexamethylenediamine, 1,2-diaminopropane, diphenylethylenediamine, diaminocyclohexane, xylylenediamines, phenylenediamine, benzidine, spermidine, spermine, toluene diamine, aminobenzylamines, and combinations thereof. In other embodiments, the polyamine is a triamine (i.e., the polyamine has three amine groups). In specific embodiments, the polyamine is a polyether diamine.

In many embodiments, the polyamine has the following general formula $R_2N$—$R^7$—$NR_2$. Each R is independently a hydrogen atom (H) or $R^1$, typically an H. $R^7$ may comprise at least one of a hydrocarbylene, a heterohydrocarbylene, or an organoheterylene group. In these embodiments, $R^7$ is typically selected from alkyl, cycloalkyl, alkyl cycloalkyl, aromatic, and alkylaromatic diradicals. Such diradicals generally have up to 50, up to 40, up to 30, up to 20, or up to 10, carbon atoms, or any number of carbon atoms between 1 and 50. The carbon chain which makes up the backbone of the polyamine may be straight chained or branched. In certain embodiments, the polyamine may have ether, thio, or amine linkages in its main chain. In specific embodiments, $R^7$ is a hydrocarbylene group having from 1 to 10 carbon atoms, or any number of carbon atoms in between.

In certain embodiments, the polyamine is a (poly)oxyalkylene compound. Suitable examples of such compounds include, but are not limited to, ethylene diamine, diethylene diamine, polyethylene diamine (e.g. having a molecular weight of 200 to 2,000), propylene diamine, dipropylene diamine, polypropylene diamine (e.g. having a molecular weight of 200 to 3,000), butylene diamine, dibutylene diamine, polybutylene diamine (e.g. having a molecular weight of 200 to 4,000), and combinations thereof.

In various embodiments, the polyamine can comprise a polyester polyamine, a polyether polyamine, a polyether/ester polyamine, or combinations thereof. Furthermore, the polyamine may be selected from aliphatic polyamines, cycloaliphatic polyamines, aromatic polyamines, heterocyclic polyamines, and combinations thereof. Some examples of suitable polyamines include, but are not limited to, glycol-initiated polyamines, glycerine-initiated polyamines, sucrose-initiated polyamines, sucrose/glycerine-initiated polyamines, trimethylolpropane-initiated polyamines, and combinations thereof.

Further examples of suitable polyamines include, but are not limited to, divalent and higher polyvalent primary or secondary, aliphatic, araliphatic, cycloaliphatic or aromatic amines. Specific examples include among others, 4-aminobenzylamines, 4,4'-diaminodicyclohexylmethane, phenylene diamines, etc. Polyamines such as diethylenetriamine, triethylenetetramine, diethylenepropylamine, N-(2-hydroxyethyl)diethylenetriamine, N,N'-di(2-hydroxyethyl)diethylenetriamine, m-phenylenediamine, methylenedianiline, aminoethyl piperazine, 4,4-diaminodiphenyl sulfone, benzyldimethylamine, dicyandiamide, and 2-methylimidazole, and triethylamine, can also be utilized.

Suitable aromatic diamines such as a diaminodiphenylsulfone, a methylenedianiline such as 4,4'-methylenedianiline, a diaminodiphenylether, benzidine, 4,4'-thiodianiline, 4-methoxy-6-m-phenylenediamine, 2,6-diaminopyridine, 2,4-toluenediamine, and dianisidine can be utilized. Further examples include alicyclic amines, such as menthane diamine and heterocyclic amines such as pyridine. In some cases, aliphatic amines such as secondary alkylamines can be utilized.

Further suitable diamines include, but are not limited to, the isomeric phenylene diamines, 4,4'-diaminobenzophenone, bis(4-amino)diphenyl ether and 2,2-bis(4-aminophenyl)propane. Other examples of suitable amines include alcohol amines, such as ethanol amine and diethanol amine, as well as amino acids and peptides.

Further examples of suitable polyamines include, but are not limited to, m-phenylenediamine, p-phenylenediamine, 4,4'-diaminodiphenyl ether, 3,4'-diaminodiphenyl ether, 4,4'-diaminodiphenylsulfone, 3,3'-diaminodiphenylsulfone, 2,2'-ditrifluoromethyl-4,4'-diaminobiphenyl, 9,9-bis(4-aminophenyl)fluorene, 9,9-bis(4-mino-3-methylphenyl)fluorene, bis[4-(4-aminophenoxy)phenyl]sulfone, bis[4-(3-aminophenoxy)phenyl]sulfone, 2,2-bis[4-(4-aminophenoxy)phenyl]propane, 3-(methylamino) propylamine, and 2,2-bis(4-aminophenyl)hexafluoropropane. Other examples include alkyl amines, propyl amine, isobutyl amine, alkyleneoxide amines, EO amines, PO amines, BO amines, etc. Combinations of different polyamines can be utilized to form the composition. Optionally, the polyamine may contain one or more Si atoms.

Third and Fourth Embodiments

In the third embodiment, the third siloxane has at least two hydroxyl groups reactive with the pendant anhydride groups of the siloxanes. In the fourth embodiment, the third siloxane has at least two amine groups reactive with the pendant anhydride groups of the siloxanes. The hydroxyl groups and/or amine groups of the third siloxanes are referred to collectively as the "functional groups". Each of the functional groups can be pendant or terminal. In various embodiments, the third siloxane has two functional groups (i.e., two hydroxyl groups or two amine groups). Typically, the third siloxane has two terminal functional groups and is free of pendant functional groups. Each of the functional groups can be directly bonded to a Si atom, or to an intervening atom or linkage that is directly bonded to a Si atom.

Each of the hydroxyl groups can be primary, secondary, or tertiary, typically primary or secondary, more typically primary. Each of the amine groups can be primary or secondary, typically primary. The functional groups are useful for reaction with the siloxanes, and can also impart additional functionality to the composition. Typically, all of the functional groups of the third siloxane cross-link with anhydride groups of the siloxanes to form linkages (e.g. ester cross-links in the case with hydroxyl groups). Some amount of anhydride and/or carboxyl groups can remain free depending on the amount of functional groups present during reaction to form the composition. Such free groups can be useful for subsequent reaction(s) and/or can also interact with substrate surfaces, e.g. skin, leather, etc.

The third siloxane can be any type of siloxane provided it has at least two functional groups reactive with the pendant anhydride groups of the siloxanes. In this way, the third siloxane serves as a cross-linker between the siloxanes to thereby form the composition. The composition may constitute just one molecule of the third siloxane, or a plurality of molecules of the third siloxane depending, for example, on the number of pendant anhydride groups attributable to the siloxanes.

In various embodiments, the third siloxane consists of siloxane bonds (Si—O—Si) within its backbone. Alternatively, the third siloxane may include siloxane bonds separated by one or more bivalent groups. Examples of suitable bivalent groups for the third siloxane are as like described for the siloxanes, e.g. —$CH_2$— linking groups. Combinations of different bivalent groups may be present within its backbone. Each of the bivalent groups may be singular or repeated. In certain embodiments, the third siloxane is a silicone diol, a silicone triol, or a silicone polyol. In other embodiments, third siloxane is a silicone diamine, a silicone triamine, or a silicone polyamine.

In various embodiments, the third siloxane comprises at least one [$SiR^8R^9$—O—] unit. In these embodiments, the third siloxane typically has repeating D units. The third siloxane also typically has terminal M units.

In certain embodiments, the third siloxane may optionally be branched, partially branched, and/or may include a resinous portion having a three-dimensional networked structure. In such embodiments, the siloxane polymer may further comprise T units, and/or Q units, and/or D units with side groups promoting such structures. Such M, D, T, and Q units can be as described for the siloxanes. In various embodiments, the third siloxane is free of T units, Q units, or both T and Q units. If the third siloxane is free of T and/or Q units, it may be referred to as a polysiloxane. If the third siloxane includes T and/or Q units, it may be referred to as a (silicone) resin.

With reference to the [$SiR^8R^9$—O—] unit, each of $R^8$ and $R^9$ can be an independently selected substituted or unsubstituted hydrocarbyl group. Examples of suitable groups for each of $R^8$ and $R^9$ are as described for $R^1$ and/or $R^4$. For example, each of $R^8$ and $R^9$ can be an alkyl group (e.g. a methyl group), an aryl group (e.g. a phenyl group), a polyether group (e.g. an EO group), etc. Each of $R^8$ and $R^9$ can the same or different.

In certain embodiments, the third siloxane is a polysiloxane of the following general formula (C):

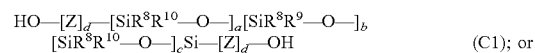

(C1); or

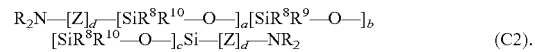

(C2).

The third siloxane of formula (C1) is an embodiment of the third embodiment. The third siloxane of formula (C2) is an embodiment of the fourth embodiment.

In formula (C), each of $R^8$ and $R^9$ are as described above. Each R is independently a hydrogen atom (H) or $R^1$; typically each R is an H. $R^{10}$ can be an independently selected substituted or unsubstituted hydrocarbyl group. Examples of suitable groups for $R^{10}$ are as described for $R^1$ and $R^4$. For example, $R^{10}$ can be an alkyl group having from 1 to 20 carbon atoms or a polyether group. In alternate embodiments, $R^{10}$ may be silicone side chain of the siloxane. The groups represented by subscripts a, b, and c, i.e., the groups having square brackets in formula (C), may be present in any order within the siloxane, including a different order than that which is represented above and throughout this disclosure. Moreover, these groups may be present in randomized or block form.

Each Z can independently comprise at least one of a hydrocarbylene, heterohydrocarbylene, or organoheterylene group. In certain embodiments, Z is a hydrocarbylene group having from 1 to 20, 1 to 10, 1 to 5, 1 to 2, 1, or 2, carbon atom(s), or any number of carbon atoms in between. Further examples of suitable groups for Z are as described with the optional bivalent groups of the siloxanes, e.g. a —CH$_2$— linking group, an EO group, a PO group, etc., or combinations thereof. In certain embodiments, the third siloxane is free of polyether groups.

Typically, a is an integer selected from 0 to 1,000, 0 to 950, 0 to 750, 0 to 500, 0 to 400, 0 to 300, 0 to 200, 0 to 100, 0 to 75, 0 to 50, 0 to 25, 0 to 20, or 0 to 15, or any number in between. Typically, b is an integer selected from 1 to 1,000, 1 to 950, 1 to 750, 1 to 500, 1 to 400, 1 to 300, or 1 to 200, or any number in between. Typically, c is an integer selected from 0 to 1,000, 0 to 950, 0 to 750, 0 to 500, 0 to 400, 0 to 300, 0 to 200, 0 to 100, 0 to 75, 0 to 50, 0 to 25, 0 to 20, or 0 to 15, or any number in between. Typically, each d is independently 0 or 1. In specific embodiments, at least one d is 1, or each d is 1.

In certain embodiments, the third siloxane is a resin of the general formula $R^*_s SiO_{(4-s)/2}$. Typically, a silicone resin will have T and/or Q units, along with M units and, optionally, D units. $R^*$ can be an independently selected substituted hydrocarbyl group, unsubstituted hydrocarbyl group, hydroxyl group, or amine group, and s is from 0 to 3. Suitable $R^*$ groups are as described for $R^8$, $R^9$, and $R^{10}$. Various combinations of such groups can be present, provided the silicone resin has at least two functional groups per molecule (typically on M units). In these embodiments, the resin generally includes a combination of M, D, T, and/or Q units. In specific embodiments, the third siloxane is a MDT resin, a MT resin, a MDQ resin, a MQ resin, or a MDTQ resin. Each of the M, D, and T units can have differing R groups. The resin can be of various molecular weights, including, but not limited to, a number average molecular weight of from 800 to 500,000, or any number in between. Other embodiments of the composition are below.

In certain embodiments, a non-functionalized resin (i.e., one lacking reactive functional groups) is utilized in the composition. In these embodiments, the non-functionalized resin is trapped within the polymeric network during cure of the composition. Such non-functionalized resins can be useful for providing chemical and/or physical modifications to the composition. Various embodiments of the composition will now be described.

The composition is generally of the following general formula (I):

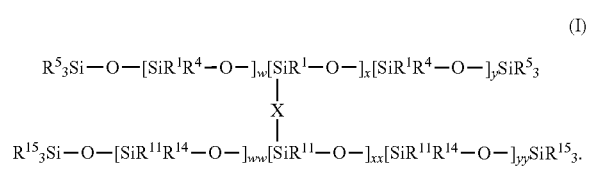

In formula (I), the upper and lower portions are attributable to the siloxanes. The siloxanes can be the same or different. $R^{11}$ can be the same as or different from $R^1$, $R^{14}$, can be as the same or different from $R^4$, and $R^{15}$ can be the same as or different from $R^5$. Typically, each $R^5$ is $R^1$, and/or each $R^{15}$ is $R^{11}$. Further, ww can be the same as or different from w, xx can be the same as or different from x, and yy can be the same as or different from y. The groups represented by subscripts w, ww, x, xx, y, and yy, i.e., the groups having square brackets in formula (I), may be present in any order within the composition, including a different order than that which is represented above and throughout this disclosure. Moreover, these groups may be present in randomized or block form.

Each of $R^1$, $R^3$, $R^4$, and $R^5$ are as like described with the siloxanes. Each of w, x, and y are also as like described with the siloxanes. Each of $R^{11}$, $R^{14}$, and $R^{15}$ can be an independently selected substituted or unsubstituted hydrocarbyl group. Examples of suitable groups for $R^{11}$, $R^{14}$, and $R^{15}$ are as described for $R^1$, $R^4$, and $R^5$.

In certain embodiments, $R^{11}$ is an independently selected alkyl group. Suitable alkyl groups can be linear, branched, or cyclic. If present as $R^{11}$, the alkyl group generally has from 1 to 20, 1 to 15, 1 to 10, 1 to 6, 1 to 4, or 1 to 2, carbon atoms, or any number of carbon atoms in between. Specific examples of suitable alkyl groups as $R^{11}$ include methyl groups, ethyl groups, propyl groups, butyl groups, pentyl groups, etc. Typically, $R^{11}$ is a methyl group.

In certain embodiments, each $R^{14}$ is an independently selected alkyl group, aryl group, or $(R^{16}O)_{mm}$ group. If $R^{14}$ is a $(R^{16}O)_{mm}$ group, $R^{16}$ is typically an alkyl group or aryl group and mm is an integer selected from 1 to 50, 1 to 25, 1 to 10, 1 to 5, or 1, or any number in between. The $(R^{16}O)_{mm}$ group may also be referred to as a polyether group. In specific embodiments, $R^{14}$ is an independently selected alkyl group having from 2 to 20, 2 to 15, 2 to 10, 2 to 5, or 2, carbon atoms, or any number of carbon atoms in between. In alternate embodiments, $R^{14}$ may be silicone side chain of the siloxane. Typically, $R^{14}$ is either an alkyl group or a polyether group.

Typically, ww is an integer selected from 0 to 1,000, 0 to 950, 0 to 750, 0 to 500, 0 to 400, 1 to 350, 1 to 300, 25 to 250, 50 to 200, 50 to 150, 75 to 125, 90 to 110, 90 to 100, or 90 to 95, or any number in between. In a specific embodiment, ww is 93. Typically, xx is an integer selected from 1 to 100, 1 to 75, 1 to 50, 1 to 25, 1 to 20, 1 to 10, or 1 to 5, or any number in between. In a specific embodiment, xx is 3. Typically, yy is an integer selected from 0 to 1,000, 0 to 950, 0 to 750, 0 to 500, 0 to 400, 1 to 350, 1 to 300, 1 to 250, 1 to 200, 1 to 150, 1 to 100, 1 to 75, 1 to 50, 1 to 25, 1 to 20, 1 to 15, 1 to 10, or 1 to 5, or any number in between.

In various embodiments, ww and yy are not simultaneously 0. In certain embodiments, the sum of ww+xx+yy is from 25 to 1,500, 25 to 1,000, 25 to 900, 25 to 800, 25 to 700, 25 to 600, 25 to 500, 25 to 400, 25 to 300, 50 to 200, 75 to 150, 85 to 125, or 90 to 110, or any number in between. In these embodiments, xx is at least 1, at least 10, at least 25, at least 50, at least 75, or at least 85.

The middle (or X) portion of formula (I) is attributable to the reactant, as well as the anhydride groups of the siloxanes. Specifically, each X is generally of the following general formula (i):

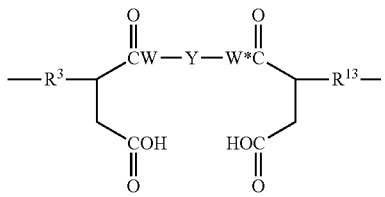

In formula (i), each of W and W* is attributable to the reactant. Typically, each of W and W* is independently an oxygen atom (O) or N—R, with R independently being a hydrogen atom (H) or $R^1$; typically R is an H. In the first and third embodiments, each of W and W* is independently an O. In the second and fourth embodiments, each of W and W* is independently N—R.

$R^{13}$ is a divalent group. Various types of divalent groups are suitable as $R^{13}$. Typically, $R^{13}$ is a hydrocarbylene, heterohydrocarbylene, or organoheterylene group. In various embodiments, $R^{13}$ is $(CH_2)_{nn}$ where nn is an integer selected from 1 to 30, 1 to 25, 1 to 20, 1 to 15, 1 to 10, 1 to 5, or 1 to 3, or any number in between. Typically, nn is 3. $R^{13}$ can be the same as or different from $R^3$.

Each Y is a divalent group, which is attributable to the reactant. In the first and second embodiments, each Y is typically an organic divalent group. During formation of the composition, the reactant had two functional groups, e.g. terminal hydroxyl groups, which reacted with pendant anhydride groups of the siloxanes to form linkages between the siloxanes and reactant.

As also shown in formula (i), the composition has two carboxyl groups. The possibility of such carboxyl groups is described below. In other embodiments (not shown), another molecule of the reactant has reacted between the two carboxyl groups to form another —Y— linkage (i.e., the two carboxyl groups in formula (i) are gone). Y can be of any structure attributable to the reactant.

In the first and second embodiments, Y typically comprises at least one of a hydrocarbylene, heterohydrocarbylene, or organoheterylene group. In certain embodiments, Y is a hydrocarbylene group having from 1 to 50, 1 to 40, 1 to 20, 1 to 20, 1 to 10, 1 to 5, 1 to 2, 1, or 2, carbon atom(s), or any number of carbon atoms in between. Further examples of suitable groups for Y are as described with the $R^7$ groups of the polyol or polyamine. In certain embodiments where the polyol or polyamine is free of polyether groups, the Y is also free of polyether groups.

In the third and fourth embodiments where the third siloxane is a polysiloxane, Y is of the following general formula (ii):

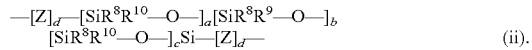

Each of $R^8$, $R^9$, $R^{10}$, and Z are as like described with the third siloxanes. Each of a, b, c, and d are also as like described with the third siloxanes. In other embodiments where the third siloxane is a resin, Y is of the general formula $R^*_s SiO_{(4-s)/2}$ where $R^*$ is an independently selected substituted hydrocarbyl group or unsubstituted hydrocarbyl group, and s is from 0 to 3.

In certain embodiments, the composition can be formed with a supplemental cross-linker in addition, and/or alternate to, the reactant. Examples of suitable supplemental cross-linkers include polyols, polyamines, polyepoxides, and combinations thereof. Suitable supplemental cross-linkers, as well as other optional components that can be used to form, and/or be used in combination with the composition, are described in U.S. Pat. No. 5,444,139 to Valpey, Ill. et al. and U.S. Pat. No. 8,026,330 to Kamei; and U.S. Pat. App. Pub. No. 2012/0040931 to Kamei; which are incorporated herein by reference.

The method comprises the steps of providing the first siloxane, providing the second siloxane, and providing the reactant. The method further comprises the step of combining the first siloxane, second siloxane, and reactant (each described above) to form the composition.

In various embodiments, the composition can be prepared by:

(1) subjecting an organohydrogensiloxane having hydrogen atoms at the site(s) where $R^2$ is to be bonded and an acid anhydride compound to an addition reaction to form the siloxanes; and (2) subjecting the siloxanes obtained in the step (1) to a ring-opening reaction by combining them with the reactant thereby forming the composition.

Suitable examples of the acid anhydride compound include, but are not limited to, succinic acid anhydride and derivatives thereof, such as vinyl succinic acid anhydride, allyl succinic acid anhydride, allyl-2-methylsuccinic acid anhydride, allyl-2,3-dimethyl succinic acid anhydride, and allyl-2-ethyl succinic acid anhydride. In various embodiments, allyl succinic anhydride (ASA) is used.

Optionally, in embodiments where the first and/or second siloxane has side chains as one or more of the $R^4$ groups, step (1) can also include providing at least one component that is reactive with hydrogen atoms at the site(s) where $R^4$ is to be bonded. Various types of components can be utilized to provide $R^4$. Typically, the component will have an unsaturated bond. Examples of suitable components include alkenes, such as those having from 2 to 20 carbon atoms; aldehydes; ketones; and combinations thereof. Specific examples of suitable alkenes include, but are not limited to, ethene, propene, 1-Butene, 1-Pentene, 1-Hexene, 1-Hexadecene, and combinations thereof. Components that impart a polyether group can be used. Vinyl terminated siloxanes may also be used as the component. Combinations of different components can be utilized to impart the $R^4$ groups. If utilized, the component can be introduced prior to, after, or simultaneously with, the acid anhydride compound. The amount of each can be tailored to impart the composition with various levels of each of the $R^2$ and $R^4$ groups. $R^4$ may already be present on the organohydrogensiloxane such that this optional step is not required.

The addition reaction in step (1) may also be referred to as a hydrosilylation reaction. The addition reaction in step (1) may be performed in the presence of catalyst, such as a platinum catalyst or a rhodium catalyst. Examples of suitable catalysts include, but are not limited to, chloroplatinic acid, chloroplatinic acid modified with an alcohol, and a complex of chloroplatinic acid with a vinylsiloxane. An amount of the catalyst to be used may be a catalytically effective amount, i.e., a catalytic amount, which is usually at most 50 ppm, particularly at most 20 ppm, as platinum metal or rhodium metal.

The addition reaction in step (1) may be performed in a solvent as needed. Various types of conventional solvents can be utilized, such as silicone solvents and/or organic solvents. A specific example of a suitable silicone solvent is 3-octylheptamethyltrisiloxane. Examples of suitable organic solvents include, but are not limited to, aromatic hydrocarbons such as toluene and xylene; aliphatic or alicyclic hydrocarbons such as n-pentane, n-hexane, and cyclohexane; and halogenated hydrocarbons such as dichloromethane, chloroform, and carbon tetrachloride. Additional examples of suitable solvents are described as "carrier fluids" in US Pat. App. Pub. No. 2010/0330011 (to Kennan et al.), which is incorporated herein by reference.

Reaction conditions for the addition reaction in step (1) are not limited to any particular ones. In certain embodiments, the addition reaction is performed under reflux for 1 to 10 hours. While step (1) is described above, the siloxanes may also be provided "as is", i.e., they need not be first formed via such an addition reaction step. Suitable siloxanes are available from Dow Corning Corporation of Midland, Mich. Suitable reactants (e.g. polyols, polyamines, and functional siloxanes) are available from a variety of sources including Dow Corning Corporation.

Optionally, rather than just cross-linking the anhydride groups of the siloxanes in step (2), one or more of the functional groups provided by the opened anhydride groups may be capped. Various types of capping components can be utilized. Typically, the capping component will have at least one functional group, e.g. a hydroxyl group, an amine group, etc. Examples of suitable capping components include branched and unbranched aliphatic, cycloaliphatic, and aromatic monols and/or monoamines. Various types of capping components can be utilized, such as those having from 1 to 20 carbon atoms. Specific examples of suitable monols include, but are not limited to, methanol, ethanol, propanol, isopropanol, butanol, sec-butanol, isobutanol, tert-butanol, and the various isomers of pentyl alcohol, hexyl alcohol, octyl alcohol (e.g. 2-ethylhexanol), nonyl alcohol, decyl alcohol (e.g. 2-propylheptanol), lauryl alcohol, myristyl alcohol, cetyl alcohol and of stearyl alcohol, as well as the fatty alcohols and wax alcohols which occur naturally or which can be obtained by the hydrogenation of naturally occurring carboxylic acids. Cyclohexanol and its homologues are examples of suitable cycloaliphatic alcohols. Further, aromatic hydroxyl compounds, such as phenol, cresol, thymol, carvacrol, benzyl alcohol and phenylethanol, can also be utilized. In certain embodiments, the capping component is selected from the group of aliphatic alcohols, such as methanol, ethanol, 2-propanol, butanol, and isodecane. Combinations of different capping components can be used. If utilized, the capping component can be introduced prior to, after, or simultaneously with, the reactant. The amount of each can be tailored to impart the composition with various levels of cross-linking, capping, free anhydride groups, and/or free carboxyl groups. Capping is optional.

The ring-opening reaction in the step (2) may be performed in a solvent as needed. Examples of suitable solvents include those listed for step (1). To prevent undesirable side-reactions/reaction-products, the solvent should be inert with respect to the reactants/reaction-intermediates. For example, the solvent shouldn't have hydroxyl or amine functional groups. This is generally true for steps (1) and (2). The reaction conditions for the ring-opening reaction are not limited to any particular ones. In certain embodiments, the ring-opening reaction is performed at a temperature of from room temperature to a reflux temperature for 1 to 10 hours.

The first siloxane, second siloxane, and reactant (collectively "the reactants") can be reacted in various amounts to form the composition. Based on the number of functional groups provided by the reactant, relative to the number of anhydride groups provided by the siloxanes, the reactants can be utilized in a 1:1 stoichiometric ratio. For example, one hydroxyl group or amine group can be present for every one of the anhydride groups present. Alternatively, the reactant can be utilized in a stoichiometric excess relative to the siloxanes. Conversely, the siloxanes can be utilized in a stoichiometric excess relative to the reactant. Such situations may also be referred to as over-indexing or under-indexing the ring-opening reaction, with an index of 1.0 (or 100) indicating that there is a stoichiometric amount of hydroxyl groups or amine groups present to react with the amount of anhydride groups present (1:1). The index may be from 0.25 to 2.0, 0.5 to 1.5, 0.9 to 1.1, 0.95 to 1.05, or 1.0, or any number in between. Higher or lower indexes may also be utilized.

Based on the particular index utilized, various situations can arise. Specifically, the composition can include various functional groups for subsequent reaction, including free carboxyl groups, and possibly even free anhydride groups and/or free hydroxyl groups and/or free amine groups, or combinations thereof. In many embodiments, the composition does not include free hydroxyl groups or free amine groups. In certain embodiments, the composition has a least two carboxyl groups. The disclosure is not limited to any particular subsequent reaction or use of such free functional groups. Various degrees of cross-linking can be present in the composition based on the index utilized to form the composition, from various degrees of partial cross-linking to full cross-linking.

In certain embodiments having free carboxyl groups after the ring-opening reaction, the composition has a carboxyl equivalent of from 100 to 50,000, 500 to 10,000, or 500 to 5,000, g/mol. For good handling property, the composition can have a viscosity of from 10 to 1,000,000, or from 10 to 100,000, mm$^2$/sec. Further, the composition can have a weight average molecular weight (reduced to polystyrene) of from 200 to 100,000, or 200 to 50,000.

The composition is useful for a variety of end applications, and is not limited to any particular one. Examples of suitable applications include use in personal care, household care, and beauty care products. Textile and coating applications are also contemplated. In embodiments having free carboxyl groups, the composition can also be used for modifying organic resins or fibers and surface-treating powder. The treated surface shows high affinity with an unctuous agent. Particularly, dispersivity of powder is significantly improved. Therefore, the composition can be useful for applications where high dispersivity of a powder is required, for example, cosmetics such as skincare and makeup products, and coatings. The composition can also be used to enhance the aesthetics of personal care formulations for skincare and healthcare by providing a unique sensory profile upon application. The composition can provide sensory characteristics such as a velvety, silky or powdery feel. In addition, the composition can be used for providing rheology modification to personal care (skin, sun, cosmetic) and healthcare formulations. The composition also has excellent formulation versatility. Without being bound or limited to any particular theory, it is thought that potential benefits provided by, or attributable to, the composition include, but are not limited to, one or more of the following: film forming, substantivity (i.e., longer lasting), durability, pigment/particle suspension and/or modification, long lasting/wear, additional chemistry, actives (e.g. drug) or inactives (e.g. fragrance) delivery/release, and combinations thereof.

The composition can also have excellent tactile aesthetic and/or rheological properties. For example, the composition can have a dry, velvety feel, which is unmatched by conventional silicone products. The composition can better anchor to skin relative to conventional products. The composition can also have excellent water uptake and/or excellent compatibility with organic solvents, such as those used in personal care applications. In various embodiments, the composition has excellent hydrophilicity, which is useful for water based or water containing formulations. Therefore, harsh or volatile carriers are unnecessary.

The following examples, illustrating the composition and method of the disclosure, are intended to illustrate and not to limit the invention.

Various examples of the siloxanes are prepared via an addition reaction scheme. These examples are described in Examples 1 through 3 below.

Example 1: Allyl Succinic Anhydride Functional (ASA) Siloxane

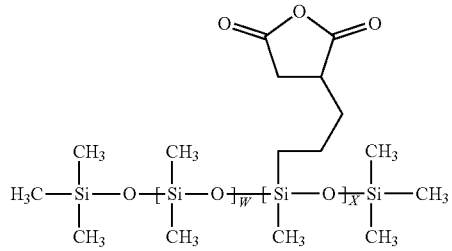

To a 1,000 ml three neck round bottom flask equipped with glass stir rod, Teflon® moon shaped paddle, stir bearing, temperature probe, heating mantle, and nitrogen sweep, is placed 311.23 grams of trimethylsilyl endblocked, dimethyl, methylhydrogen siloxane ($MD_{93}D^H{}_6M$), 38.77 grams of ASA ($C_7H_8O_3$), and 50.0 grams of toluene (solvent). The contents of the reaction flask are heated to 70° C. and catalyzed with 5 ppm platinum IV. The addition reaction exotherms and the flask is held at 80° C. for two hours. The reactants are then stripped with a 2 inch POPE Scientific Inc. Thin Film Stripper at 170° C. and 0.1 mm Hg to remove toluene and other volatiles.

Example 2: ASA Siloxane Finished with 1-Hexene

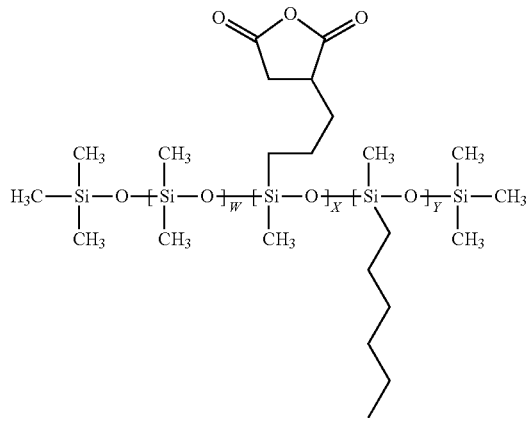

To a 500 ml three neck round bottom flask equipped with glass stir rod, Teflon® moon shaped paddle, stir bearing, temperature probe, heating mantle, and nitrogen sweep, is placed 229.23 grams of trimethylsilyl endblocked, dimethyl, methylhydrogen siloxane ($MD_{93}D^H{}_6M$), 20.77 grams of ASA ($C_7H_8O_3$), and 100.0 grams of isododecane (solvent). The contents of the reaction flask are heated to 70° C. and catalyzed with 5 ppm platinum IV. The addition reaction exotherms and the flask is held at 80° C. for two hours. To the flask is added 4.0 grams of 1-Hexene to finish the reaction. The reactants are then stripped with a 2 inch POPE Scientific Inc. Thin Film Stripper at 170° C. and 0.1 mm Hg to remove isododecane and other volatiles. The reaction is 61% ASA and 39% 1-Hexene according to 13C NMR/FTIR.

Example 3: ASA Siloxane Finished with 1-Hexadecene

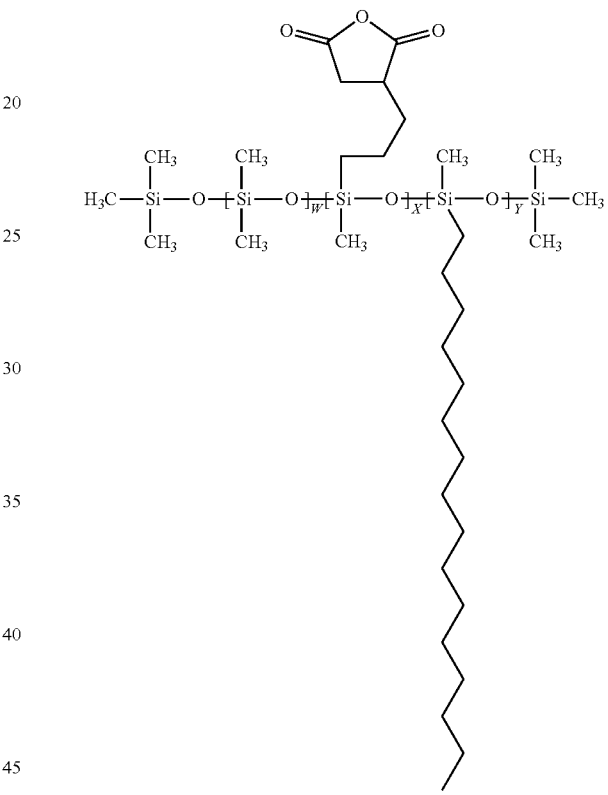

To a 500 ml three neck round bottom flask equipped with glass stir rod, Teflon® moon shaped paddle, stir bearing, temperature probe, heating mantle, and nitrogen sweep, is placed 94.15 grams of trimethylsilyl endblocked, dimethyl, methylhydrogen siloxane ($MD_{93}D^H{}_6M$), 5.86 grams of ASA ($C_7H_8O_3$), and 100.0 grams of isododecane (solvent). The contents of the reaction flask are heated to 70° C. and catalyzed with 5 ppm platinum IV. The addition reaction exotherms and the flask is held at 80° C. for two hours. To the flask is added 6.78 grams of 1-Hexadecene to finish the reaction. The reactants are then stripped with a 2 inch POPE Scientific Inc. Thin Film Stripper at 170° C. and 0.1 mm Hg to remove isododecane and other volatiles. The reaction is 50% ASA and 50% 1-Hexadecene according to 13C NMR/FTIR.

Embodiments of the disclosure utilizing different reactants are described below. Specifically, various examples of the composition are prepared via a ring-opening reaction scheme. These examples are described in Examples 4 through 16 below.

First Embodiment

Example 4: ASA Siloxane and PEG

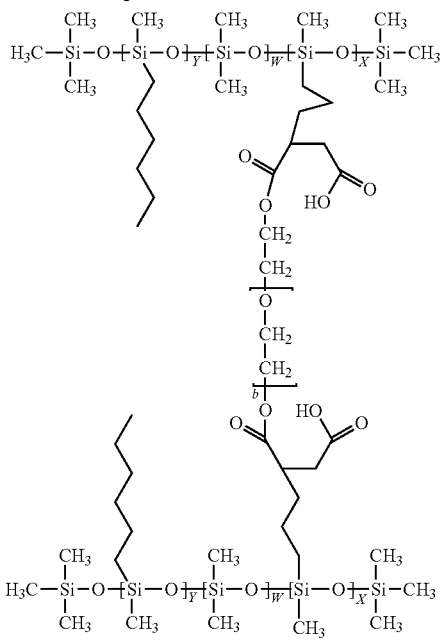

14.46 grams of ASA siloxane, 0.54 grams of poly(ethyleneglycol) with an average molecular weight of 200, and 15.0 grams of isododecane (solvent) are added to a 4 oz olive jar equipped with magnetic star shaped stirrer. The olive jar is placed into a water bath at 70° C. The water bath is positioned above a magnetic stirrer hot plate. The magnetic stirrer is set to setting four and the sample begins to gel. After approximately one hour, the reaction gel is placed in an oven at 70° C. for three hours. The sample is then removed from the oven and allowed cool to room temperature.

Example 5: ASA Siloxane and Diol

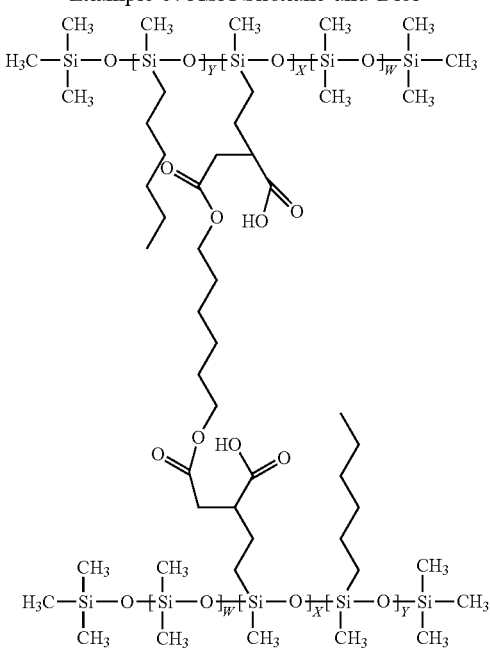

9.75 grams of ASA siloxane from Example 2, and 0.42 grams of 1,6 hexanediol are added to a 4 oz olive jar equipped with magnetic star shaped stirrer. The olive jar is placed into a water bath at 75° C. After the diol melts, the reaction mixture gels in thirty minutes. The mixture is a clear hard solid. The mixture is allowed to cure at 75° C. for three hours. The jar is then removed from the water bath and allowed to cool to room temperature.

Example 6: ASA Siloxane and Diol in Presence of Solvent

This example is similar to example 5, but includes a solvent. 29.25 grams of ASA siloxane, 1.26 grams of 1,6 hexanediol, and 30.51 grams of isododecane (solvent) are added to a 4 oz olive jar equipped with magnetic star shaped stirrer. The olive jar is placed into a water bath at 75° C. After the diol melts, the reaction mixture gels in 60 minutes. The mixture is a clear hard solid. The mixture is allowed to cure at 75° C. for three hours. The jar is then removed from the water bath and allowed to cool to room temperature.

Example 7: ASA Siloxane and PAG

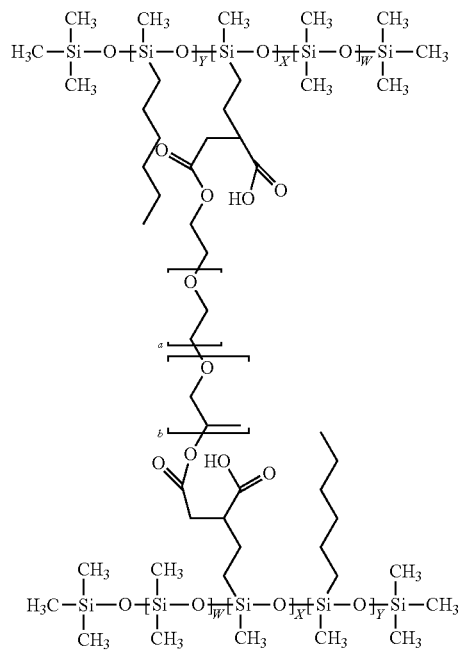

18.74 grams of ASA siloxane from Example 2, 6.25 grams of a polyalkylene glycol, and 25.0 grams of isododecane (solvent) are added to a 4 oz olive jar equipped with magnetic star shaped stirrer. The olive jar is placed into a water bath at 75° C. The reaction mixture gels in several hours. The mixture is a clear solid. The mixture is allowed to cure at 75° C. for three hours. The jar is then removed from the water bath and allowed to cool to room temperature.

Example 8: ASA Siloxane, Monol, and Diol

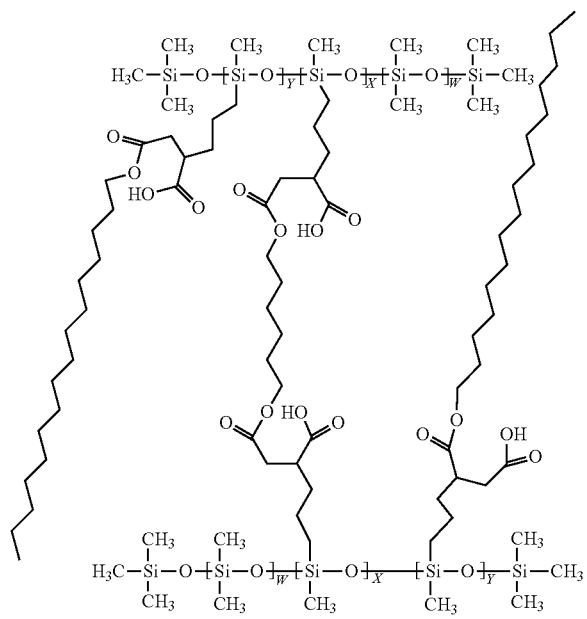

29.25 grams of ASA siloxane, 1.26 grams of 1-Hexadecanol, and 30.51 grams of isododecane (solvent) are added to a 4 oz olive jar equipped with magnetic star shaped stirrer. The olive jar is placed into a water bath at 75° C. Next, 0.88 grams of 1,6 hexanediol are added to the jar. After the diol melts, the reaction mixture gels in 60 minutes. The mixture is a clear gel. The mixture is allowed to cure at 75° C. for three hours. The jar is then removed from the water bath and allowed to cool to room temperature.

Second Embodiment

Example 9: ASA Siloxane and 1,8-diaminooctane

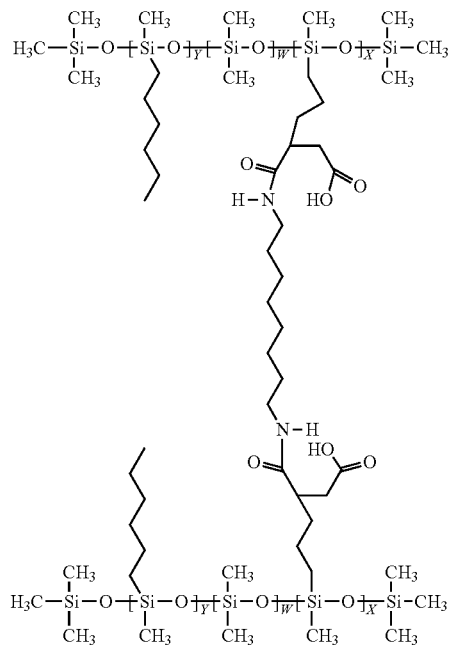

14.61 grams of ASA siloxane from Example 2, 0.39 grams of 1,8-diaminooctane, and 15.0 grams of isododecane (solvent) are added to a 8 oz olive jar equipped with magnetic star shaped stirrer. The olive jar is placed into a water bath at 70° C. The water bath is positioned above a magnetic stirrer hot plate. The magnetic stirrer is set to setting four and the sample begins to gel. After formation, the reaction gel is placed in an oven at 70° C. for three hours. The sample is then removed from the oven and allowed cool to room temperature.

Example 10: ASA Siloxane and Poly(Ethylene Glycol)Diamine

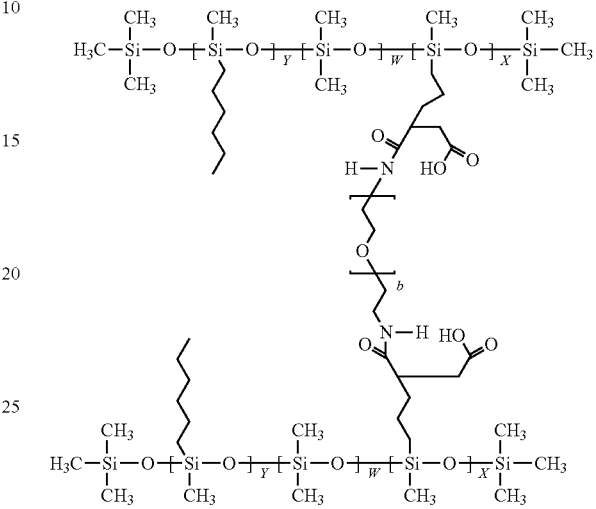

18.24 grams of ASA siloxane from Example 2, 6.76 grams of poly(ethylene glycol)diamine, and 25.0 grams of isododecane (solvent) are added to a 4 oz olive jar equipped with magnetic star shaped stirrer. The olive jar is placed into a water bath at 70° C. The water bath is positioned above a magnetic stirrer hot plate. The magnetic stirrer is set to setting four and the sample begins to gel. After formation, the reaction gel is placed in an oven at 70° C. for three hours. The sample is then removed from the oven and allowed cool to room temperature.

Example 11: ASA Siloxane and 1,5 diamino-2-methylpentane

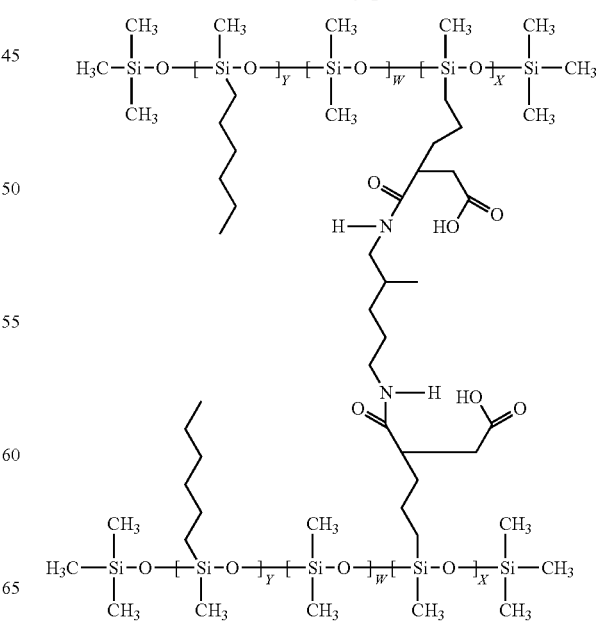

24.48 grams of ASA siloxane from Example 2, 0.52 grams of 1,5 diamino-2-methylpentane, and 25.0 grams of isododecane (solvent) are added to a 4 oz olive jar equipped with magnetic star shaped stirrer. The olive jar is placed into a water bath at 70° C. The water bath is positioned above a magnetic stirrer hot plate. The magnetic stirrer is set to setting four and the sample begins to gel. After formation, the reaction gel is placed in an oven at 70° C. for three hours. The sample is then removed from the oven and allowed cool to room temperature.

Third Embodiment

Example 12: ASA Siloxane and Hydroxyl Terminated Siloxane

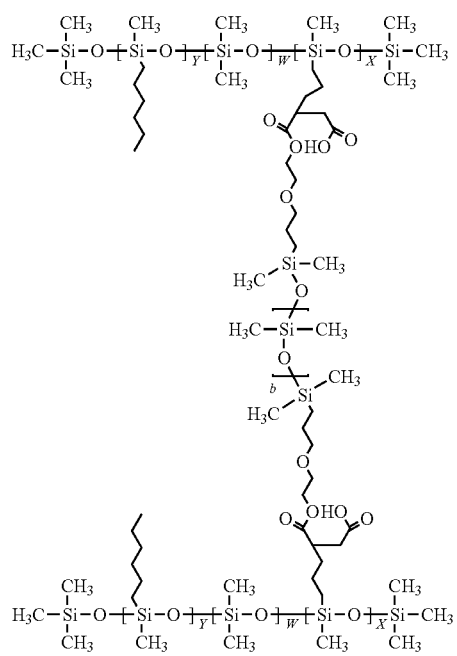

17.56 grams of ASA siloxane from Example 2, 4.5 grams of dimethyl siloxane, dimethyl (3-(2-hydroxyethyl)propyl-ether))siloxy-terminated, and 22.0 grams of isododecane (solvent) are added to a 4 oz olive jar equipped with magnetic star shaped stirrer. The olive jar is placed into a water bath at 70° C. The water bath is positioned above a magnetic stirrer hot plate. The magnetic stirrer is set to setting four and the sample begins to gel. After approximately one hour, the reaction gel is placed in an oven at 70° C. for three hours. The sample is then removed from the oven and allowed cool to room temperature.

Example 13: ASA Siloxane and Hydroxyl Terminated Siloxane

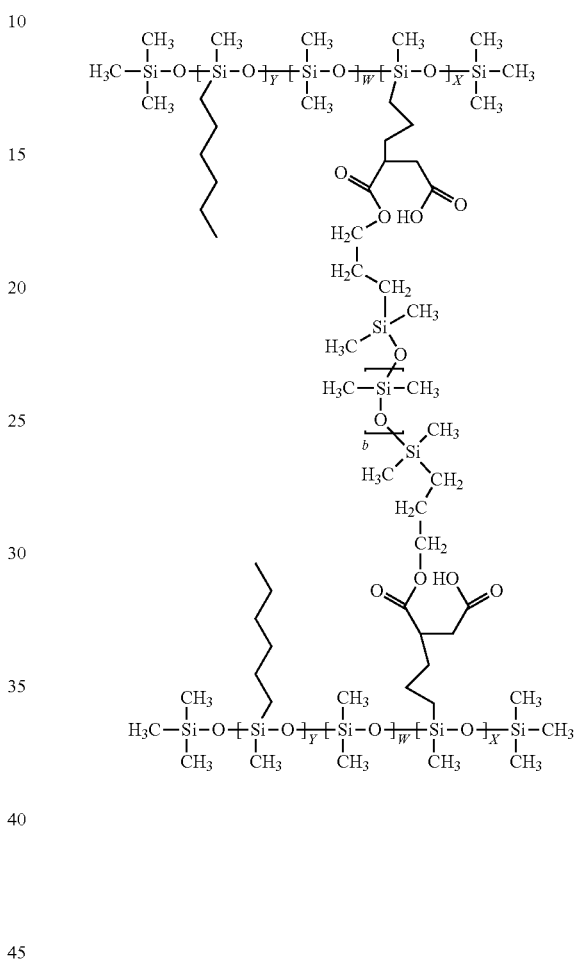

12.76 grams of ASA siloxane from Example 2, 2.24 grams of dimethyl siloxane, 3-hydroxypropyl terminated, and 15.0 grams of isododecane (solvent) are added to a 4 oz olive jar equipped with magnetic star shaped stirrer. The olive jar is placed into a water bath at 70° C. The water bath is positioned above a magnetic stirrer hot plate. The magnetic stirrer is set to setting four and the sample begins to gel. After approximately one hour, the reaction gel is placed in an oven at 70° C. for three hours. The sample is then removed from the oven and allowed cool to room temperature.

Example 14: ASA Siloxane and Hydroxyl Terminated Siloxane

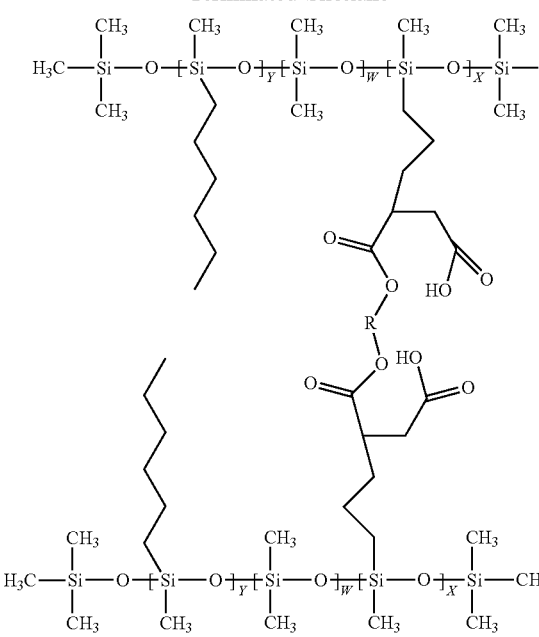

R =

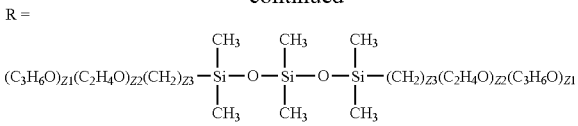

32.87 grams of ASA siloxane from Example 2, 17.13 grams of dimethyl, methyl(propyl(poly(EO)(PO))hydroxyl) siloxane, trimethylsiloxy terminated, and 50.0 grams of isododecane (solvent) are added to a 4 oz olive jar equipped with magnetic star shaped stirrer. The olive jar is placed into a water bath at 70° C. The water bath is positioned above a magnetic stirrer hot plate. The magnetic stirrer is set to setting four and the sample begins to gel. After approximately one hour, the reaction gel is placed in an oven at 70° C. for three hours. The sample is then removed from the oven and allowed cool to room temperature.

Example 15: ASA Siloxane and Hydroxyl Terminated Siloxane; Under Indexed/Partially Reacted

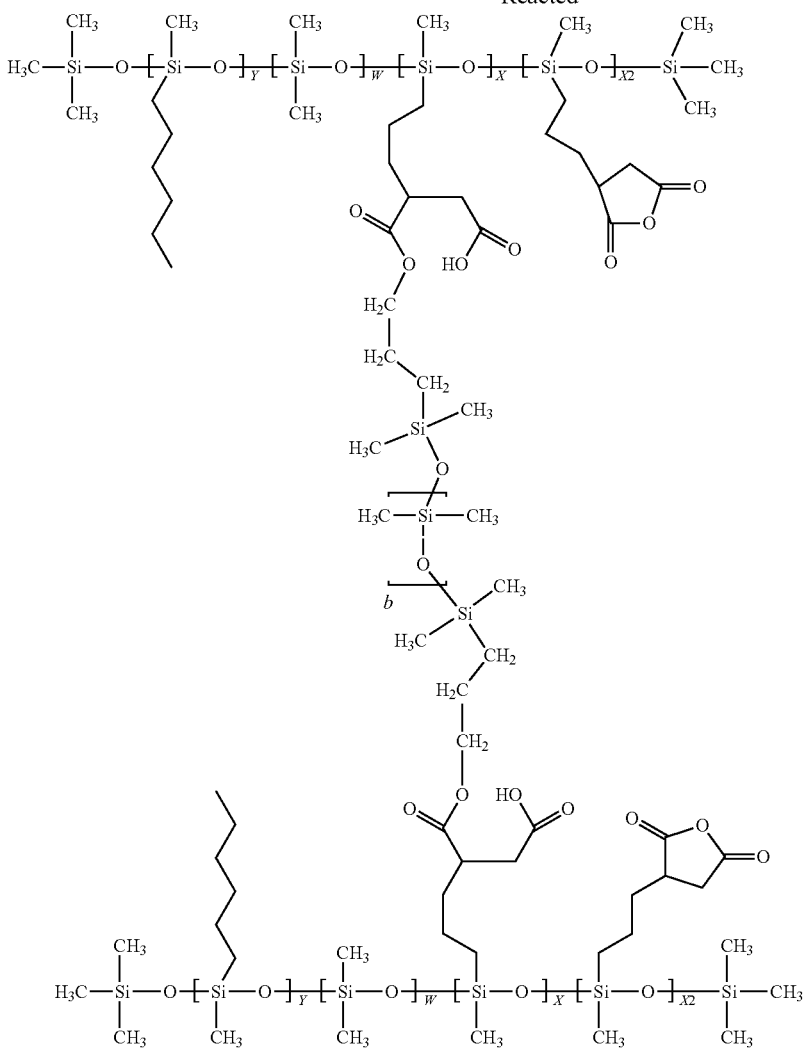

36.03 grams of ASA siloxane from Example 2, 13.97 grams of dimethyl siloxane, 3-hydroxypropyl terminated, and 50.0 grams of 3-octylheptamethyltrisiloxane (solvent) are added to a 4 oz olive jar equipped with magnetic star shaped stirrer. The olive jar is placed into a water bath at 70° C. The water bath is positioned above a magnetic stirrer hot plate. The magnetic stirrer is set to setting four and the sample begins to gel. After approximately one hour, the reaction gel is placed in an oven at 70° C. for three hours. The sample is then removed from the oven and allowed cool to room temperature.

Fourth Embodiment

Example 16: ASA Siloxane and Aminopropyl Endblocked Siloxane

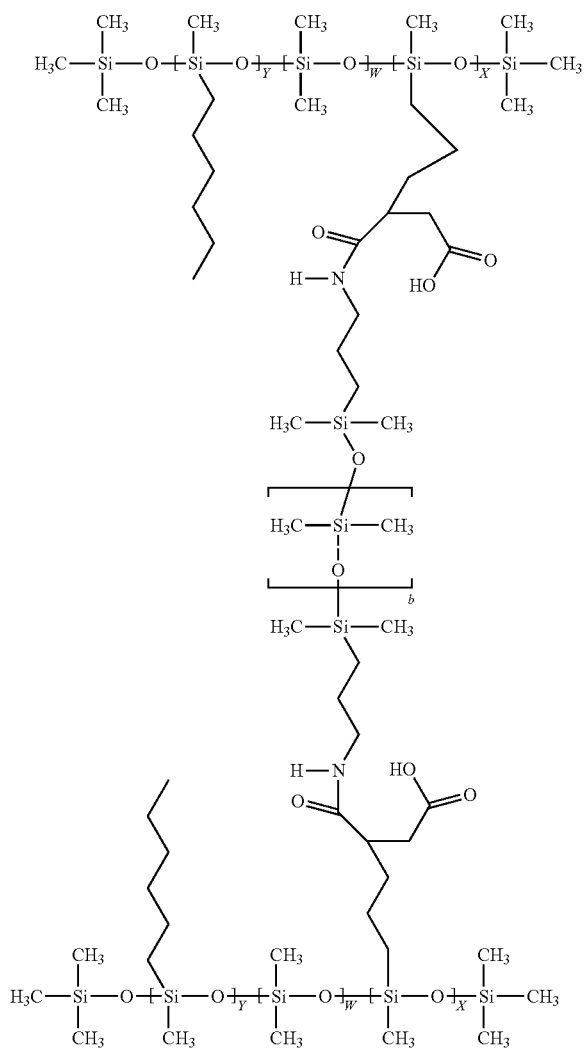

12.72 grams of ASA siloxane from Example 2, 12.28 grams of aminopropyl endblocked dimethyl siloxane, and 75.0 grams of 3-octylheptamethyltrisiloxane (solvent) are added to a 4 oz olive jar equipped with magnetic star shaped stirrer. The olive jar is placed into a water bath at 70° C. The water bath is positioned above a magnetic stirrer hot plate. The magnetic stirrer is set to setting four and the sample begins to gel. After approximately one hour, the reaction gel is placed in an oven at 70° C. for three hours. The sample is then removed from the oven and allowed cool to room temperature.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

What is claimed is:

1. A cross-linked composition comprising the reaction product of:
   a first siloxane having at least one pendant anhydride group;
   a second siloxane having at least one pendant anhydride group; and
   a reactant comprising a polyol having at least two carbon-bonded hydroxyl groups reactive with the pendant anhydride groups of said first and second siloxanes.

2. The cross-linked composition as set forth in claim 1, wherein said polyol is selected from the group of:
   i) an organic polyol having at least two carbon-bonded hydroxyl groups reactive with the pendant anhydride groups of said first and second siloxanes;
   ii) a third siloxane having at least two carbon-bonded hydroxyl groups reactive with the pendant anhydride groups of said first and second siloxanes;
   iii) combinations thereof.

3. The cross-linked composition as set forth in claim 2, wherein said polyol is said organic polyol and wherein:
   i) said organic polyol has two terminal carbon-bonded hydroxyl groups;
   ii) said organic polyol is free of silicon; or
   iii) both i) and ii).

4. The cross-linked composition as set forth in claim 2, wherein said polyol is said third siloxane and said third siloxane has two terminal carbon-bonded hydroxyl groups.

5. The cross-linked composition as set forth in claim 1, wherein each of said first and second siloxanes comprise at least one [SiR$^1$R$^2$—O—] unit, R$^1$ is an independently selected substituted or unsubstituted hydrocarbyl group, R$^2$ is a pendant anhydride group of the following general formula (A):

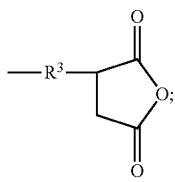

(A)

and R$^3$ is a divalent group.

6. The cross-linked composition as set forth in claim 5, wherein each of said first and second siloxanes is individually of the following general formula (B):

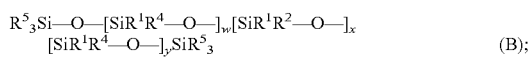

(B);

each of R$^1$ and R$^2$ are as defined above, alternatively each R$^1$ is an independently selected alkyl group; R$^3$ is a hydrocarbylene, heterohydrocarbylene, or organoheterylene group, alternatively R$^3$ is (CH$_2$)$_n$ where n is an integer selected from 1 to 30; R$^4$ is a substituted or unsubstituted hydrocarbyl group, alternatively R$^4$ is an independently selected alkyl group, aryl group, or polyether group; each R$^5$ is an independently selected substituted or unsubstituted hydrocarbyl group, alternatively each R$^5$ is R$^1$; w is an integer selected from 0 to 1,000, alternatively 1 to 300; x is an integer selected from 1 to 100, alternatively 1 to 75; and y is an integer selected from 0 to 1,000, alternatively 1 to 300; with the proviso that w and y are not simultaneously 0.

7. The cross-linked composition as set forth in claim 6, wherein each of said first and second siloxanes is individually of the following general formula (B1):

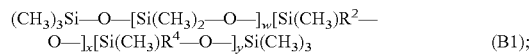

(B1);

R$^3$ of R$^2$ is (CH$_2$)$_n$ where n is an integer selected from 1 to 15, alternatively 3; R$^4$ is an independently selected alkyl group having from 2 to 20 carbon atoms; w is an integer selected from 50 to 200, alternatively 75 to 125; x is an integer selected from 1 to 50, alternatively 1 to 5; and y is an integer selected from 1 to 200, alternatively 1 to 5.

8. The cross-linked composition as set forth in claim 1, wherein said polyol has the following general formula: HO—R$^7$—OH; where R$^7$ comprises at least one of a hydrocarbylene, a heterohydrocarbylene, or an organoheterylene group, alternatively is a hydrocarbylene group having from 1 to 40 carbon atoms, alternatively 1 to 10 carbon atoms.

9. The cross-linked composition as set forth in claim 2, wherein said reaction product is further derived from a polyamine having at least two amine groups reactive with the pendant anhydride groups, and/or derivatives thereof, of said first and second siloxanes.

10. The cross-linked composition as set forth in claim 2, wherein said polyol comprises said third siloxane and said third siloxane is a polysiloxane of the following general formula:

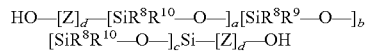

wherein each of R$^8$, R$^9$, and R$^{10}$ is an independently selected substituted or unsubstituted hydrocarbyl group; each Z independently comprises at least one of a hydrocarbylene, heterohydrocarbylene, or organoheterylene group, alternatively each Z is a hydrocarbylene group having from 1 to 20 carbon atoms; a is an integer selected from 0 to 1,000; b is an integer selected from 1 to 200; c is an integer selected from 0 to 1,000, alternatively 0 to 400; and each d is 1.

11. The cross-linked composition as set forth in claim 3, wherein:
   i) said organic polyol has two terminal carbon-bonded hydroxyl groups; and
   ii) said organic polyol is free of silicon.

12. The cross-linked composition as set forth in claim 1, wherein said polyol is a polyether diol.

13. A cross-linked composition of the following general formula (I):

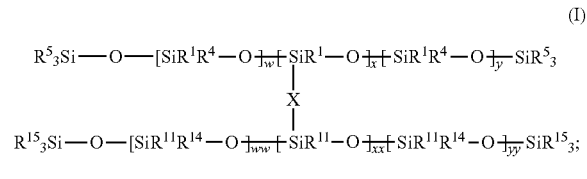

(I)

wherein X is of the following general formula (i);

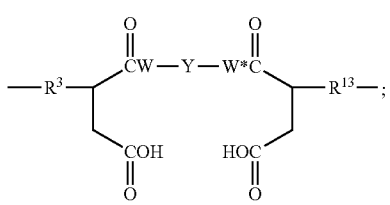

each of W and W* is an oxygen atom (O); each Y is a divalent group; each of $R^1$, $R^{11}$, $R^4$, $R^{14}$, $R^5$, and $R^{15}$ is an independently selected substituted or unsubstituted hydrocarbyl group; each of $R^3$ and $R^{13}$ is an independently selected divalent group; each of w and ww is an independently selected integer from 0 to 1,000; each of x and xx is an independently selected integer from 1 to 100; and each of y and yy is an independently selected integer from 0 to 1,000; with the provisions that w and y are not simultaneously 0, and ww and yy are not simultaneously 0; and wherein Y is a divalent group formed from a polyol having at least two carbon-bonded hydroxyl groups.

14. The cross-linked composition as set forth in claim 13, wherein each of $R^1$ and $R^{11}$ is an independently selected alkyl group; $R^3$ is $(CH_2)_n$ where n is an integer selected from 1 to 30, alternatively 1 to 15; $R^{13}$ is $(CH_2)_{nn}$ where nn is an integer selected from 1 to 30, alternatively 1 to 15; each $R^4$ is an independently selected alkyl group, aryl group, or polyether group, alternatively each $R^4$ is an independently selected alkyl group having from 2 to 20 carbon atoms; each $R^{14}$ is an independently selected alkyl group, aryl group, or polyether group, alternatively each $R^{14}$ is an independently selected alkyl group having from 2 to 20 carbon atoms; each $R^5$ is $R^1$; each $R^{15}$ is $R^{11}$; each of w and ww is an independently selected integer from 1 to 300, alternatively 75 to 125; each of x and xx is an integer selected from 1 to 75, alternatively 1 to 5; and each of y and yy is an integer selected from 1 to 300, alternatively 1 to 5.

15. The cross-linked composition as set forth in claim 13, wherein Y comprises at least one of a hydrocarbylene, heterohydrocarbylene, or organoheterylene group.

16. The cross-linked composition as set forth in claim 13, wherein Y is of the following general formula (ii):

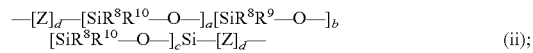

wherein each of $R^8$, $R^9$, and $R^{10}$ is an independently selected substituted or unsubstituted hydrocarbyl group; Z comprises at least one of a hydrocarbylene, heterohydrocarbylene, or organoheterylene group; a is an integer selected from zero to 1,000; b is an integer selected from 1 to 200; c is an integer selected from 0 to 400; and each d is 1.

17. The cross-linked composition as set forth in claim 13, wherein said polyol has the following general formula: HO—$R^7$—OH; where $R^7$ comprises at least one of a hydrocarbylene, a heterohydrocarbylene, or an organoheterylene group, alternatively is a hydrocarbylene group having from 1 to 40 carbon atoms, alternatively 1 to 10 carbon atoms.

18. The cross-linked composition as set forth in claim 13, wherein said polyol is a polyether diol.

19. The cross-linked composition as set forth in claim 13, wherein said polyol comprises a polysiloxane of the following general formula:

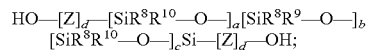

wherein each of $R^8$, $R^9$, and $R^{10}$ is an independently selected substituted or unsubstituted hydrocarbyl group; each Z independently comprises at least one of a hydrocarbylene, heterohydrocarbylene, or organoheterylene group, alternatively each Z is a hydrocarbylene group having from 1 to 20 carbon atoms; a is an integer selected from 0 to 1,000; b is an integer selected from 1 to 200; c is an integer selected from 0 to 1,000, alternatively 0 to 400; and each d is 1.

20. The cross-linked composition as set forth in claim 1, having:
   i) free carboxyl groups and optionally, free anhydride groups, provided by said first and/or second siloxane (s);
   ii) a carboxyl equivalent of from 100 to 50,000 g/mol; or
   iii) both i) and ii).

* * * * *